Figure 1:

| United States Patent [19] | [11] | 4,148,690 |
|---|---|---|
| Weetall | [45] | Apr. 10, 1979 |

[54] BIOPHOTOLYSIS OF WATER

[75] Inventor: Howard H. Weetall, Big Flats, N.Y.

[73] Assignee: Corning Glass Works, Corning, N.Y.

[21] Appl. No.: 855,359

[22] Filed: Nov. 28, 1977

Related U.S. Application Data

[63] Continuation-in-part of Ser. No. 771,945, Feb. 25, 1977, abandoned.

[51] Int. Cl.² ........................... C12B 1/00; C12K 1/00
[52] U.S. Cl. ...................................... 195/115; 47/1.4; 195/104; 195/127; 195/142
[58] Field of Search ............... 195/115, 127, 142, 139, 195/116, 104, 103.5 R; 47/1.4

[56] References Cited

U.S. PATENT DOCUMENTS 4,010,076  3/1977  Weetall ............................ 195/127 X Primary Examiner—Raymond N. Jones
Assistant Examiner—Robert J. Warden
Attorney, Agent, or Firm—William E. Maycock; Clinton S. Janes, Jr.

[57] ABSTRACT

Method for continuous production of $H_2$ via the biophotolysis of water in a two step process using a reversibly reduceable cofactor and synergistic photometabolically active microorganisms. The rate of $H_2$ production can be increased utilizing transition metal ions as catalysts.

25 Claims, 6 Drawing Figures

BIOPHOTOLYSIS OF WATER

This application is a continuation-in-part of Ser. No. 771,945, filed Feb. 25, 1977, now abandoned.

Related Application

Patent application Ser. No. 672,631 filed Apr. 1, 1976 in the name of H. H. Weetall, entitled "Reactor for Stabilized Microbes Having Photometabolic Activity", now U.S. Pat. No. 4,010,076, and assigned to the same assignee as this application.

BACKGROUND OF THE INVENTION

1. Field

This disclosure is concerned generally with the field of fermentation and specifically with the use of photometabolically active microorganisms to produce molecular hydrogen from water.

2. Prior Art

As pointed out in the above-cited patent, the disclosures of which are incorporated herein by reference thereto, it is well known that certain microorganisms are capable of producing useful products in the presence of light and certain substrates. The disclosed photometabolically active systems are concerned primarily with using a single type of microorganism to produce products such as $H_2$, ATP, and NADPH on a continuous basis. Although multiple organism systems are disclosed, no actual examples are shown.

Thus, that patent generally describes a method for the continuous photometabolic production of a useful product which consists in immobolizing whole cells of a photometabolically active organism on a medium to form a stabilized composite, supportably placing the composite within a reactor having at least one light transmitting wall, and, in the presence of light being transmitted through the wall, continuously passing into the reactor a substance capable of being photometabolized by the cells under conditions sufficient to assure the production of the useful product. The specification discloses two particularly preferred inventive embodiments. In the first, an aqueous malate solution constitutes the substance being photometabolized, molecular hydrogen as the product being formed, bacterial cells as the whole cells, and the immobilizing medium as a gel-like material. In the second, Blue-Grass algae are similarly stabilized for the continuous biophotolysis of water by oxidizing the water and reducing NADP to NADPH. In those preferred embodiments, *Rhodospirillium rubrum* comprise the operable bacterial cells, *Anacystis nidulans* constitute the operable algae cells, and agar provides the operable gel-like material.

In work done subsequent to that which was the basis for the above application, I have found an improved method for the biophotolysis of water and the production of $H_2$ gas. This method is based on the use of two systems of microorganisms and the continuous recycling of a reduceable cofactor such as nicotine-adenine-dinucleotide phosphate (NADP) through both systems. Details of the method are described below.

SUMMARY OF THE INVENTION

The process for the biophotolytic production of molecular hydrogen from water on a continuous basis comprises the steps of reacting an aqueous solution of a reversibly reduceable cofactor in the presence of light with a preparation of a first photometabolically active microorganism under conditions sufficient to reduce at least a portion of the cofactor X to form HX in the solution; reacting the solution of HX in the presence of light with a preparation of a second photometabolically active microorganism capable of oxidizing the HX and releasing molecular hydrogen; collecting the released hydrogen; and returning the solution to the first microorganism. The two microorganisms are kept separate and, with respect to the biophotolysis of water to form $H_2$, are synergistic. In preferred embodiments, the separate preparations of microorganisms are confined to a fixed location within an essentially closed, continuous reaction system capable of exposing both preparations to light energy as the aqueous solution of cofactor is continuously passed in an essentially closed circuit over or through both preparations of microorganisms. In very preferred embodiments, the aqueous solution of the reduced cofactor is reacted with the second preparation of microorganisms under essentially anaerobic conditions by using, for example, an oxygen scavenger system within the overall system. At appropriate points in the system, provision is made for the collection of $H_2$ and the replenishing of any reagents.

It is possible to significantly increase the production rate of molecular hydrogen and improve the energy efficiency of the process, both in the instant inventive process and in the single system for producing molecular hydrogen described in U.S. Pat. No. 4,010,076, through the use of transition metal ions as catalysts. As employed herein, the operable transition metal ions include those elements having atomic numbers ranging from 22-29, inclusive, of the Periodic Table.

SPECIFIC EMBODIMENTS

A very important part of the improved method for the photometabolic or biophotolytic conversion of water into hydrogen (and oxygen) is the microorganism which, in the presence of light and a reduceable cofactor material X, is capable of biophotolytically degrading water. Organisms having such capability are well known (see U.S. Pat. No. 4,010,076) and include algae such as *Anacystis nidulans*. That organism is capable of reducing an aqueus solution of a cofactor such as NADP to NADPH in the presence of light. Although the exact mechanism is not known with certainty, it is known that the reaction of an aqueous solution of NADP with organisms such as *A. nidulans* will release oxygen and reduce at least some of the NADP to NADPH. As a consequence of the above reaction, the aqueous solution contains less NADP (or more NADPH) than before the reaction; thereby resulting in an increase in the overall ratio of NADPH to NADP. This increase in the ratio of NADPH to NADP can then be exploited to produce molecular hydrogen by reacting the solution containing the increased ratio of NADPH to NADP (excess NADPH) in the presence of light with a second microorganism for which the amount of NADPH present is in excess of cellular needs.

Thus, while the single system for producing $H_2$ described in U.S. Pat. No. 4,010,076 was capable of forming $H_2$ gas via the photometabolic action on a given substrate such as a malate solution, the present dual system requires only NADPH (preferably an amount in excess of cellular needs) for the production of $H_2$. Thus, the dual system approach is highly significant for a continuous system since it permits the recycling of what is the more expensive reagent (the NADP). The less expensive reagent (water) is degraded (and easily replaced) rather than a more expensive substrate such as the cofactor or past substrates such as the malate. Thus, it can be appreciated that unlike past methods for producing $H_2$ (e.g. U.S. Pat. No. 4,010,076), the present method provides a NADPH-rich environment prior to reaction with the organism capable of ultimately releasing $H_2$ from an aqueous solution of NADPH. By assuring an environment of NADPH in excess of the cellular requirements of the organism, an overall increased amount of $H_2$ gas results.

As used therein, the expression photometabolism or its equivalents refers to the use of light energy (visible electromagnetic radiation) as one of the driving energy forces in biochemical reactions, especially by microorganisms having the ability to biochemically utilize light energy. The terms microorganism, microbes, organisms and the like, as used herein, refer to basically unicellular organisms such as algae, bacteria and the like, all of which are recognized as having the property of photometabolism. The expression biophotolysis or its equivalent, as used herein, refers to a type of photometabolism in which light is the driving force to degrade or break down a product and form a useful product. The term cofactor, as used herein, refers to a substance capable of being reduced in the presence of one microorganism type and oxidized to release $H_2$ gas in the presence of another microorganism type. The expression preparation of microorganism or its equivalent, as used herein, refers to the confinement of a given microorganism to a fixed location within a continuous flow system. In preferred embodiments, microorganism preparations are composites of microbes fixed to the surfaces of high surface area supports. The expression $O_2$ scavenger or its equivalent, as used herein, refers to any means for removing dissolved oxygen from an aqueous solution, which means are not detrimental to living microorganisms in communication with the solution. Typical $O_2$ scavengers include $O_2$ permeable membranes, the use of enzymes such as glucose oxidase alone or in combination with other enzyme systems such as catalase, and the like. $O_2$ scavengers are used to minimize or eliminate $O_2$ and the adverse effects of $O_2$ on certain microorganisms, especially anaerobes.

Figure 2:
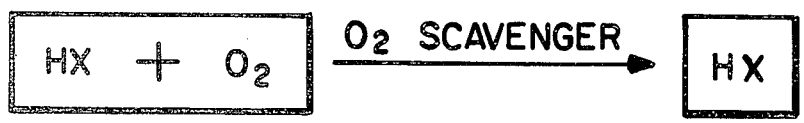
Figure 3:

The overall process of this disclosure is illustrated in FIGS. 1-4. FIG. 1 shows an initial reaction of an aqueous solution of a reduceable cofactor X in the presence of light and a first photometabolically active microbe (e.g. algae) to degrade water and reduce the X to HX. In the reactions of FIGS. 1-3, the reactions are not intended to be balanced. In FIG. 2, the reaction product of the first step, an aqueous solution containing HX and dissolved $O_2$, is contacted with an $O_2$ scavenger, if needed, to remove substantially all dissolved $O_2$. In FIG. 3, the aqueous solution of HX is reacted in the presence of light with a second photometabolically active microbe (e.g. bacteria) to release $H_2$ gas which can be conveniently collected prior to return of the aqueous solution to the first microbe preparation.

Figure 4:
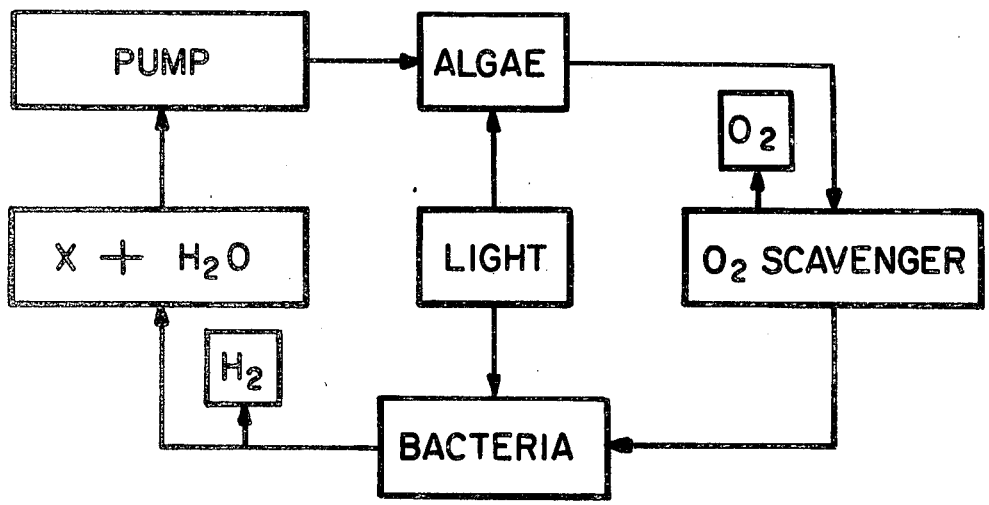

In FIG. 4, the overall process is illustrated as an essentially closed system in which both the first and second microbe preparations are exposed to light while an aqueous solution containing the X and/or HX is continuously pumped through and in intimate contact with the microbe preparations. In the illustrative examples below, the cofactor reducing microbe preparation comprised a composite of the algae *Anacystis nidulans* and agar which was spread over plates placed within a transparent flow through reactor. The $H_2$ releasing microbe comprised a similar composite of the bacteria *Rhodospirillium rubrum* and agar. Both microbe preparations were made as shown in U.S. Pat. No. 4,010,076 and placed in flow through reactors described in detail in that patent. It can be appreciated, however, that the microbe preparations can be made in other ways as long as they permit intimate reaction with a solution of the cofactor or reduced cofactor in the presence of light in a continuous flow-through situation.

The $O_2$ scavenger system used in the illustrative examples below involved adding the enzyme glucose oxidase (1mg per ml of solution) to the reaction solution. That enzyme allows the removal of dissolved $O_2$, forming $H_2O_2$. The $H_2O_2$ is easily removed by passing the flow through solution through a bed of immobilized catalase (catalase fixed on surfaces of high surface area porous glass particles). The catalase converts the $H_2O$ back to $O_2$ at a convenient $O_2$ collection point, e.g., a gas trap above the immobillized catalase bed.

Although the system described below was an essentially closed system which lessened the chance of dissolution of atmospheric air into the flow through solution, at one point, prior to passage of the solution over and through the algae preparation, a beaker containing a reservoir of the solution was subjected to an argon purge by bubbling a stream of argon into the solution and letting the gas rise up through the solution and out of the beaker, thereby precluding the entrance of atmospheric $O_2$. This system allowed the convenient replenishing of substances such as water or the glucose oxidase.

EXAMPLE I

A system similar to that illustrated in FIG. 4 was set up. Two grams each of the algae *A. nidulans* and the bacteria *R. rubrum* were separately immobilized in agar as described in U.S. Pat. No. 4,010,076 and placed in separate transparent reactors as described in that disclosure. A stock solution of 500 ml of water containing 1 $\mu$mole/ml of NADP was placed in a solution reservoir having an inlet and outlet. The outlet communicated with the algae reactor inlet, the algae reactor outlet communicated with the bottom of a column (1.5 = 15 cm) containing 1.0 g of the immobilized catalase. This column was adapted to receive the solution from the algae reactor and pass it through the fixed bed of catalase to release upwardly escaping gases ($O_2$). At the bottom of the column was an outlet in communication with the inlet of the bacteria reactor. Near the outlet of that reactor, $H_2$ gas was collected as in U.S. Pat. No. 4,010,076 and the solution (containing less NADPH and more NADP) was passed back into the solution reservoir from which it was passed back into the algae reactor. A simple pump (e.g. peristaltic) can be positioned at any convenient point in the system. The 500 ml of aqueous substrate containing the 1 $\mu$mole/ml of NADP were continuously circulated at 8.0 ml/hr at 15° C. for the times shown below. The collected $H_2$ gas was determined by gas chromatography and periodically recorded as indicated Light energy was provided by exposing the reactors to 6 incandescent light bulbs, 100 watts each, positioned about 6 inches from the transparent walls of each reactor. It can be appreciated that other light sources, including solar, are possible and that various methods can be readily devised for maximizing exposure of a given microbe preparation to the light source.

Figure 5:
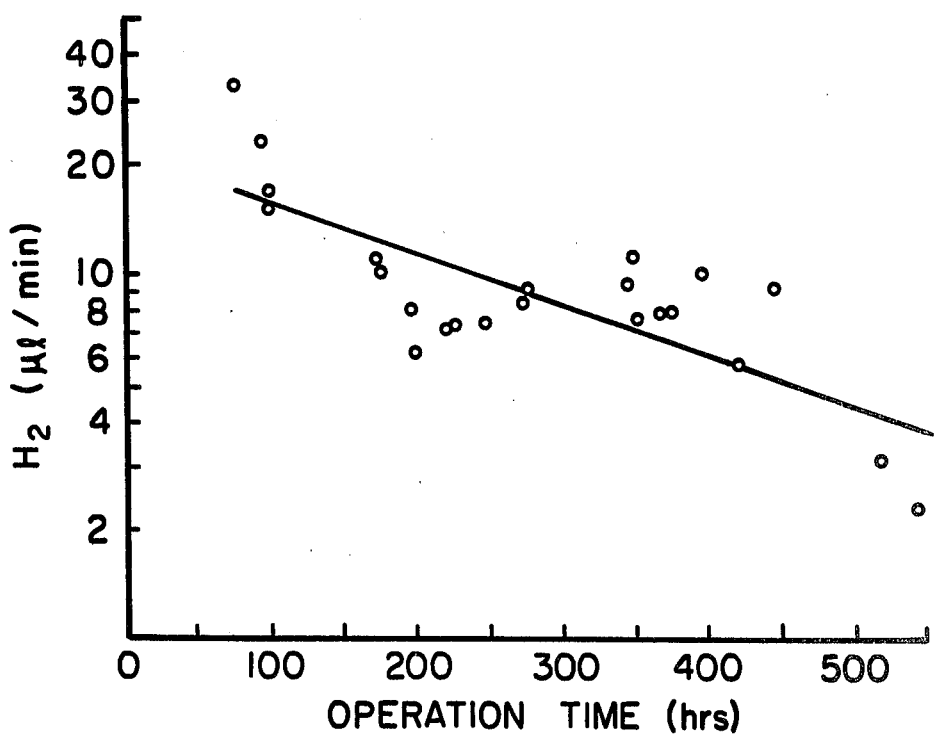
Figure 6:
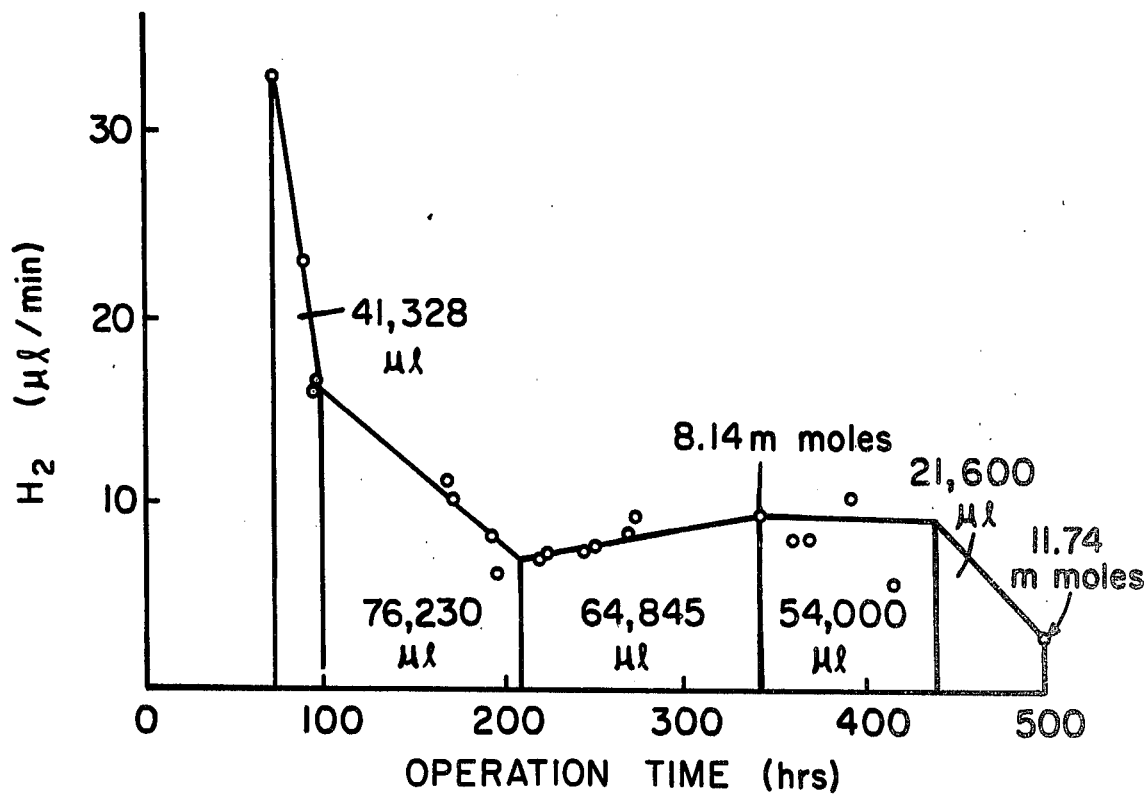

The results of operation over a 500 hour period are shown in FIGS. 5 and 6. The total H₂ produced was 11.74 m moles (millimoles). Since the concentration of the NADP was one μ mole (micromole) per ml, 500 μ moles of NADP were used to produce 11,740 μ moles of H₂. See FIG. 6. By assuming each turn over of 2 NADP molecules produced 1 H₂, NADP turned over 47 times. Regarding the data of FIG. 5, the half life ($T_{\frac{1}{2}}$) of the system was found to be 216.7 hours with an upper 95% confidence limit of 345.8 hours and a lower 95% confidence limit of 157.8 hours. Standard error was 0.36 and correlation was 0.77.

Control

A control experiment was set up leaving out the algae reactor and using only the R. rubrum reactor as described above and in U.S. Pat. No. 4,010,076. The same aqueous substrate (500 ml of water containing 500 μg NADP) was circulated in the same manner through the reactor which was exposed to the same light source. The results are summarized in the Table below.

TABLE

| Operation Time (hrs.) | H₂ Produced (μl) |
|---|---|
| 22 | 4.56 |
| 124 | 2.62 |
| 147 | 3.53 |
| 170 | 10.6 |
| 290 | 2.05 |
| 334 | 0.14 |

Compared with the production rate of the dual system example above, at 334 hours the difference is approximately 75 times. This clearly shows that the addition of a second reactor system (in this case the algae) is preferred for long term H₂ production. Although the exact mechanism is not fully understood, the H₂ produced by the control system may be related to the ability of the organism to convert metabolites to some organic acid or acids capable of conversion by the organism to H₂ gas.

Investigation has shown that the presence of transition metal ions in both the instant inventive process and the single system for producing molecular hydrogen described in U.S. Pat. No. 4,010,076 can significantly expedite the rate of hydrogen production in each. The transition metals which can be operable in both practices consist of those elements of the Peridic table having atomic numbers ranging from 22–29, inclusive, viz., Ti, V, Cr, Mn, Fe, Co, Ni, and Cu.

Although the mechanism by which those metals increase the production rate of molecular hydrogen is not fully understood, it is believed that their function is akin to a catalyst since their presence is not discerned in the reaction products. The following discussion is presented as an attempt to explain the action of these ions in the reactions taking place in the two inventive processes.

The photosynthesis of hydrogen is believed to most probably occur via the following series of linked oxidation-reduction reactions. Photosynthetic processes take place within organellae known as plastids. The primary process is though to be the absorption of sunlight leading to the phosphorylation of ADP with inorganic phosphate to produce ATP. Thus, $$h\nu + +Pi + ADP \rightarrow ATP$$

Malate from the citrate cycle is oxidized to oxalacetate with concomitant reduction of NAD⁺ to NADH with ATP as the energy source. The NAD⁺/NADH system is linked to the NADP⁺/NADPH system which is, in turn, linked to ferridoxin where molecular hydrogen formation occurs (D'Eustachio, A. J. and Hardy, R. W. F., Biochem. Biophys. Res. Comm., 15, 319 (1964). Those processes can be illustrated schematically as:

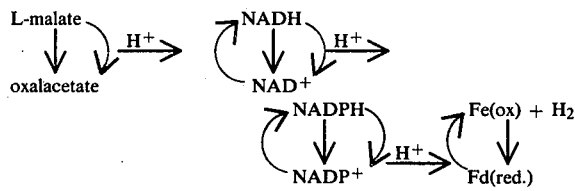

Transition metal ions may interact in several places in this complex set of reactions. Furthermore, those ions may also reduce the energy requirements for the formation of activated complexes. Still another possibility is that those ions enhance the membrane permeability for the malate substrate (Chibata, J., Tosa, T., Sato, T., Mori, T., and Yamamoto, K. Enzyme Engineering, 2, E. K. Pye and L. B. Wingard, J., Ed., Plenum Press, p. 303 (1974).

The following example is provided to demonstrate the dramatic effect which the inclusion of transition metal ions has upon the rate of molecular hydrogen production in the dual system method of the instant invention.

EXAMPLE II

Two runs were made wherein the system and reagents employed in Example I were utilized. In one run, however, labeled Run B, 0.001 M MnCl₂ was dissolved in the NADP stock solution to a pH of 6.8. The two runs were conducted in the manner described in Example I with the following results:

| Parameters | Run A | Run B |
|---|---|---|
| Operation Time | 535 hours | 96 hours |
| $T_{\frac{1}{2}}$ | 181 hours | 30.4 hours |
| 95% Upon Confidence Level | 280 hours | 41.6 hours |
| 95% Lower Confidence Level | 134 hours | 23.9 hours |
| Correlation | 0.83 | 0.94 |
| Total H₂ Produced | 0.978 moles/m² | 0.836 moles/m² |
| Energy Input | $1.83 \times 10^6$ joules | $3.28 \times 10^5$ joules |
| Usable Energy Recovered from H₂ Produced | $2.88 \times 10^3$ joules | $2.46 \times 10^3$ joules |
| Energy Efficiency | 0.157% | 0.75% |
| Average Daily Production Rate of H₂ Assuming 15 Hours of Daylight | 0.03 moles/m² | 0.13 moles/m² |

It is believed that these data make evident that not only does the presence of the manganese ions substantially increase the rate of molecular hydrogen production, but also significantly improves the energy efficiency of the process.

In order to illustrate that the catalytic effect of the transition metal ions is also active in the single system described in U.S. Pat. No. 4,010,076, the following work was undertaken. The general process steps and transparent flow through reactor apparatus disclosed in U.S. Pat. No. 4,010,076 were employed.

EXAMPLE III

Four grams of concentrated *Rhodospirillium rubrum* wet weight were blended into 15 ml of a 5% by weight solution of Noble Agar. The resultant mixture was spread evenly on both sides of a plastic slab. The slab was placed into an airtight transparent system and 0.01M malate solution, continually purged with argon, was passed through the system in an upward flow of 8 ml/hour. The system was immersed in a water bath maintained at a temperature of 18°–19° C. The gas evolved was channeled to a double-ended glass tube, serving as a collector, which was kept airtight by septums consisting of two serum vial tops. The malate solution was pulled through the collector with a syringe displacing any gas with substrate. Collection of the produced gas displaced the liquid. A sample was taken after the gas and the malate equilibrated and then a constant flow rate was re-established. Illumination of the coated plastic slab was provided via a rack of seven 100 watt standard incandescent bulbs on each side of the reactor. The bulbs were positioned about two inches from the water bath containing the reactor such as to be at a perpendicular distance of about 4–5 inches from the slab coated with the film of immobilized organisms.

The method for assaying the immobilized *R. rubrum* involved the following procedure. A volume of 0.75 ml of gas was withdrawn from the collector. From that amount 0.5 ml was injected into a Tracor 550 Gas chromatograph. The quantity of molecular hydrogen produced (measured in $\mu l$) was determined from a standard curve prepared with pure hydrogen. The percentage of hydrogen in the 0.5 ml sample was then calculated. The final quantity of molecular hydrogen was delineated in terms of $\mu l$ $H_2$ produced per minute at a constant flow rate of 8 ml/hour.

Two runs were made. In the first, 0.001M $MnCl_2$ solution was added to the malate solution to a pH of 6.8 and, in the second run, 0.001M $CuCl_2$ was added to the malate solution to a pH of 6.8. The results are reported in the table below.

| Run with $MnCl_2$ | |
|---|---|
| Time of Run in Hours | Hydrogen Production $\mu l$/min |
| 4 | 130.00 |
| 25 | 320.00 |
| 31 | 228.50 |
| 50 | 211.30 |
| 54 | 128.50 |
| 70 | 99.90 |
| 75 | 70.50 |
| 90 | 25.00 |

| Run with $CuCl_2$ | |
|---|---|
| Time of Run in Hours | Hydrogen Production $\mu l$/min |
| 18 | 69.07 |
| 23 | 61.40 |
| 43 | 43.20 |
| 46 | 33.30 |

In U.S. Pat. No. 4,010,076, it was observed that where the parameters of Example III were followed except for the addition of the transition metal ions to the two runs above. the maximum $H_2$ production was typically about 22.01 $\mu l H_2$/minute.

The above figures leave no doubt of the vast increase in the rate of hydrogen production which the inclusion of transition metal ions can impart.

Given the above disclosures and those in U.S. Pat. No. 4,010,076 it is thought that numerous variations of the dual system for the biophotolysis of water to form $H_2$ gas are now possible. Accordingly, it is intended that the specific systems described above should be deemed as illustrative only and that the scope of this invention should be limited only by the following claims.

I claim:

1. A process for the continuous photometabolic production of molecular hydrogen from water which comprises the steps of:
   (a) continuously reacting an aqueous solution of a reversibly reduceable cofactor in the presence of light with a preparation of a photometabolically active preparation of a first microorganism under conditions sufficient to reduce at least a portion of the cofactor in the solution;
   (b) reacting the reaction product of step (a) in the presence of light with a photometabolically active preparation of a second microorganism capable of oxidizing the reduced cofactor and releasing molecular hydrogen into the solution;
   (c) collecting the molecular hydrogen released in step (b); and
   (d) returning the solution to the microorganism preparation of step (a).

2. The process of claim 1 wherein the photometabolically active organism of step (a) is an algae.

3. The process of claim 1 wherein the algae is *Anacystis nidulans*.

4. The process of claim 1 wherein the photometabolically active organism of step (b) is a bacterium.

5. The process of claim 4 wherein the bacterium is *Rhodospirillum rubrum*.

6. The process of claim 1 wherein an oxygen scavenging step is used prior to step (b).

7. A dual reactor system for the continuous photometabolic production of molecular hydrogen from water comprising in combination:
   (a) a first reactor comprising a hollow body having an inner chamber and means in the body for transmitting light from a source external to the reactor to the inner chamber, inlet and outlet passageways in communication with the inner chamber and the environment external to the body and, disposed within the chamber and in communication with said inlet and outlet passageways, means retaining a photometabolically active preparation of microorganisms capable of reducing a reduceable cofactor in an aqueous solution;
   (b) a second reactor comprising a hollow body having an inner chamber and means in the body for transmitting light from a source external to the reactor to the inner chamber, inlet and outlet passageways communicating with the inner chamber and environment external to the body and, disposed within the chamber and in communication with the inlet and outlet passageways means retaining a photometabolically active preparation of microorganisms capable of oxidizing a reduced cofactor in an aqueous solution and thereby releasing molecular hydrogen into the solution;
   (c) means for continuously passing an aqueous solution of the reversibly reduceable cofactor into the inlet passageway of the first reactor, through that reactor, and then through the inlet passageway of the second reactor, through that reactor and back to the inlet passageway of the first reactor;

(d) means for providing light through the light transmitting means of both reactors; and (e) means for continuously collecting the molecular hydrogen released by the microbe preparation of the second reactor.

8. The reactor system of claim 7 wherein oxygen scavenger means are disposed in a position prior to the inlet of the second reactor.

9. The reactor system of claim 7 wherein microorganism preparation of the first reactor comprises a mixture of a gel-like material and an algae.

10. The reactor system of claim 9 wherein the algae is *Anacystis nidulans*.

11. The reactor system of claim 7 wherein the microorganism preparation of the second reactor comprises a mixture of a gel-like material and a bacterium.

12. The reactor system of claim 11 wherein the bacterium is *Rhodospirillum rubrum*.

13. In a process for the continuous photometabolic production of molecular hydrogen from water comprising the steps of:

(a) continuously reacting an aqueous solution of a reversibly reduceable cofactor in the presence of light with a preparation of a photometabolically active preparation of a first microorganism under conditions sufficient to reduce at least a portion of the cofactor in the solution;

(b) reacting the reaction product of step (a) in the presence of light with a photometabolically active preparation of a second microorganism capable of oxidizing the reduced cofactor and releasing molecular hydrogen into the solution;

(c) collecting the molecular hydrogen released in step (b); and (d) returning the solution to the microorganism preparation of step (a);

the improvement which comprises adding transition metal ions selected from the group of Ti, V, Cr, Mn, Fe, Co, Ni, Cu, and mixtures thereof to said aqueous cofactor solution.

14. The process of claim 13 wherein the photometabolically active organism of step (a) is an algae.

15. The process of claim 14 wherein the algae is *Anacystis nidulans*.

16. The process of claim 13 wherein the photometabolically active organism of step (b) is a bacterium.

17. The process of claim 16 wherein the bacterium is *Rhodospirillium rubrum*.

18. In a method for the continuous photometabolic production of a useful product comprising the steps of immobilizing whole cells of a photometabolically active organism on a medium to form a stabilized composite, supportably placing the composite within a reactor having at least one light transmitting wall, and, in the presence of light being transmitted through the wall, continuously passing into the reactor a substance capable of being photometabolized by the cells under conditions sufficient to assure the production of the useful product, the improvement which comprises adding transition metal ions selected from the group of Ti, V, Cr, Mn, Fe, Co, Ni, Cu, and mixtures thereof to said substance capable of being photometabolized.

19. The method of claim 18 wherein the whole cells are bacterial cells.

20. The method of claim 19 wherein the bacterial cells are cells of *Rhodospirillium rubrum* and the medium on which the cells are immobilized is a gel-like material.

21. The method of claim 20 wherein the gel-like material is agar.

22. The method of claim 21 wherein the substance being photometabolized is an aqueous malate solution and the product produced is molecular hydrogen.

23. The method of claim 18 wherein the whole cells are algae cells.

24. The method of claim 23 wherein the algae cells are cells of *Anacystis nidulans* and the medium on which the cells are immobilized is a gel-like material.

25. The method of claim 24 wherein the gel-like material is agar.

* * * * *

UNITED STATES PATENT AND TRADEMARK OFFICE
CERTIFICATE OF CORRECTION

PATENT NO. : 4,148,690
DATED : April 10, 1979
INVENTOR(S) : Howard H. Weetall

It is certified that error appears in the above–identified patent and that said Letters Patent are hereby corrected as shown below:

Column 4, line 18, change "$H_2O-$" to -- $H_2O_2$ -- .

Column 5, line 46, change "Peridic" to -- Periodic -- .

Signed and Sealed this

Sixteenth Day of October 1979

[SEAL]

Attest:

RUTH C. MASON
Attesting Officer

LUTRELLE F. PARKER
Acting Commissioner of Patents and Trademarks